US008555875B2

(12) United States Patent
Cook et al.

(10) Patent No.: US 8,555,875 B2
(45) Date of Patent: Oct. 15, 2013

(54) INHALATION DEVICES AND RELATED METHODS FOR ADMINISTRATION OF SEDATIVE HYPNOTIC COMPOUNDS

(75) Inventors: Robert Owen Cook, Hillsborough, NJ (US); Thomas A Armer, Cupertino, CA (US)

(73) Assignee: Map Pharmaceuticals, Inc., Mountain View, CA (US)

(*) Notice: Subject to any disclaimer, the term of this patent is extended or adjusted under 35 U.S.C. 154(b) by 511 days.

(21) Appl. No.: 12/655,076

(22) Filed: Dec. 21, 2009

(65) Prior Publication Data
US 2010/0192945 A1 Aug. 5, 2010

Related U.S. Application Data

(60) Provisional application No. 61/203,560, filed on Dec. 23, 2008.

(51) Int. Cl.
*A61M 11/00* (2006.01)

(52) U.S. Cl.
USPC .................................................. 128/200.23

(58) Field of Classification Search
USPC ............. 128/200.23, 200.14, 203.15, 200.24; 424/45, 46
See application file for complete search history.

(56) References Cited

U.S. PATENT DOCUMENTS

| | | | |
|---|---|---|---|
| 3,454,701 A | 7/1969 | Zeile et al. | |
| 3,632,345 A | 1/1972 | Marx et al. | |
| 3,987,052 A | 10/1976 | Hester, Jr. | |
| 4,375,473 A | 3/1983 | Rudzik | |
| 4,382,938 A | 5/1983 | Kaplan et al. | |
| 4,460,592 A | 7/1984 | Kaplan et al. | |
| 4,492,695 A | 1/1985 | Kaplan et al. | |
| 4,508,726 A | 4/1985 | Coleman | |
| 4,544,664 A | 10/1985 | Karjalainen et al. | |
| 4,587,257 A | 5/1986 | DeSantis et al. | |
| 4,626,538 A | 12/1986 | Dusza et al. | |
| 4,670,455 A | 6/1987 | Virtanen et al. | |
| 4,878,903 A * | 11/1989 | Mueller ........................ 604/199 | |
| 4,910,214 A | 3/1990 | Karjalainen et al. | |
| 5,212,196 A | 5/1993 | House et al. | |
| 5,484,607 A | 1/1996 | Horacek | |
| 5,496,537 A | 3/1996 | Henry | |
| 5,804,587 A | 9/1998 | Cupps et al. | |
| 5,914,342 A | 6/1999 | Maurer et al. | |
| 5,916,900 A | 6/1999 | Cupps et al. | |
| 5,954,047 A | 9/1999 | Armer et al. | |
| 5,965,595 A | 10/1999 | Maurer et al. | |
| 6,026,808 A | 2/2000 | Armer et al. | |
| 6,034,239 A | 3/2000 | Ohkawa et al. | |
| 6,036,239 A | 3/2000 | Hammersley | |
| 6,095,141 A | 8/2000 | Armer et al. | |
| 6,110,952 A | 8/2000 | Henry et al. | |
| 6,117,871 A | 9/2000 | Maurer et al. | |
| 6,162,818 A | 12/2000 | Henry et al. | |
| 6,172,095 B1 | 1/2001 | Cupps et al. | |
| 6,225,331 B1 | 5/2001 | Cupps et al. | |
| 6,242,460 B1 | 6/2001 | Ettema et al. | |
| 6,306,877 B1 | 10/2001 | Cupps et al. | |
| 6,319,926 B1 | 11/2001 | Cotrel et al. | |
| 6,348,485 B1 | 2/2002 | Ohkawa et al. | |
| 6,367,471 B1 | 4/2002 | Genosar et al. | |
| 6,391,878 B2 | 5/2002 | Cupps et al. | |
| 6,395,764 B1 | 5/2002 | Henry et al. | |
| 6,423,724 B1 | 7/2002 | Cupps et al. | |
| 6,436,978 B1 | 8/2002 | Cupps et al. | |
| 6,444,673 B1 | 9/2002 | Cotrel et al. | |
| 6,514,531 B1 * | 2/2003 | Alaux et al. ................... 424/468 |
| 6,638,535 B2 * | 10/2003 | Lemmens et al. ............. 424/489 |
| 6,716,415 B2 | 4/2004 | Rabinowitz et al. | |
| 6,716,867 B1 | 4/2004 | Aantaa et al. | |
| 6,814,955 B2 | 11/2004 | Rabinowitz et al. | |
| 6,864,257 B2 | 3/2005 | Cotrel et al. | |
| 7,001,609 B1 | 2/2006 | Matson et al. | |
| 7,040,314 B2 | 5/2006 | Nguyen et al. | |
| 7,078,017 B2 * | 7/2006 | Rabinowitz et al. ............. 424/45 |
| 7,125,874 B2 | 10/2006 | Cotrel et al. | |
| 7,381,724 B2 | 6/2008 | Cotrel et al. | |
| 7,445,768 B2 | 11/2008 | Rabinowitz et al. | |
| 7,494,998 B2 * | 2/2009 | Coughlin et al. ......... 514/254.02 |
| 7,524,864 B2 * | 4/2009 | Edgar et al. ................... 514/320 |
| 2001/0000345 A1 | 4/2001 | Cupps et al. | |
| 2002/0028950 A1 | 3/2002 | Cupps et al. | |
| 2002/0072527 A1 | 6/2002 | Aslam et al. | |
| 2002/0095039 A1 | 7/2002 | Cupps et al. | |
| 2002/0128481 A1 | 9/2002 | Cupps et al. | |
| 2003/0017116 A1 | 1/2003 | Rabinowitz et al. | |
| 2003/0077227 A1 | 4/2003 | Dugger, III | |

(Continued)

FOREIGN PATENT DOCUMENTS

| | | | |
|---|---|---|---|
| EP | 0 944 601 B1 | 2/2003 | |
| EP | 0 944 621 B1 | 9/2004 | |

(Continued)

OTHER PUBLICATIONS

Anonymous. (1999-2011). "Dexmedetomidine," located at <http://www.demedetomidine.com>, last visited on Mar. 16, 2011, 1 page.
Anonymous. (Mar. 2001). "Special Report: Current Strategies in ICU Sedation," *Sponsored by the Dannemiller Memorial Educational Foundation* pp. 1-8.
Gertler, R. et al. (Jan. 2001). "Dexmedetomidine: A Novel Sedative-Analgesic Agent," *Baylor University Medical Center Proceedings* 14(1):13-21.
Groeben, H. et al. (Feb. 2004). "Effects of the α2-Adrenoceptor Agonist Dexmedetomidine on Bronchoconstriction in Dogs," *Anesthesiology* 100(2):359-363.

(Continued)

*Primary Examiner* — Manuel Mendez
(74) *Attorney, Agent, or Firm* — Jennifer C. Cheng

(57) ABSTRACT

An inhalation device for administering one or more sedatives via pulmonary delivery for treating a sleep disturbance.

23 Claims, No Drawings

(56) References Cited

U.S. PATENT DOCUMENTS

| | | |
|---|---|---|
| 2003/0181354 A1 | 9/2003 | Abdulrazik |
| 2004/0081624 A1 | 4/2004 | Nguyen et al. |
| 2004/0096402 A1 | 5/2004 | Hodges et al. |
| 2004/0099269 A1 | 5/2004 | Hale et al. |
| 2004/0151670 A1 | 8/2004 | Blondino et al. |
| 2004/0228807 A1 | 11/2004 | Rabinowitz et al. |
| 2004/0265239 A1 | 12/2004 | Dugger, III et al. |
| 2004/0265242 A1 | 12/2004 | Bartus et al. |
| 2005/0089479 A1 | 4/2005 | Rabinowitz et al. |
| 2005/0129621 A1 | 6/2005 | Davies et al. |
| 2005/0222270 A1 | 10/2005 | Olney et al. |
| 2006/0032501 A1 | 2/2006 | Hale et al. |
| 2006/0063827 A1 | 3/2006 | Yu et al. |
| 2006/0120962 A1 | 6/2006 | Rabinowitz et al. |
| 2006/0159624 A1 | 7/2006 | Dugger, III et al. |
| 2006/0198896 A1 | 9/2006 | Liversidge et al. |
| 2006/0199805 A1 | 9/2006 | Pyke et al. |
| 2006/0216240 A1 | 9/2006 | Dugger, III et al. |
| 2006/0239928 A1 | 10/2006 | Heit et al. |
| 2007/0049576 A1 | 3/2007 | Barlow et al. |
| 2007/0060501 A1 | 3/2007 | Jhamandas et al. |
| 2007/0078083 A1 | 4/2007 | Barlow et al. |
| 2007/0081948 A1 | 4/2007 | Morton et al. |
| 2007/0112017 A1 | 5/2007 | Barlow et al. |
| 2007/0208029 A1 | 9/2007 | Barlow et al. |
| 2007/0213411 A1 | 9/2007 | Francis et al. |
| 2007/0219185 A1 | 9/2007 | Kobayashi et al. |
| 2007/0244143 A1 | 10/2007 | Barlow et al. |
| 2007/0256688 A1 | 11/2007 | Schuster et al. |
| 2007/0270449 A1 | 11/2007 | Barlow et al. |
| 2007/0299135 A1 | 12/2007 | Martin et al. |
| 2008/0008748 A1 | 1/2008 | Beyreuther et al. |
| 2008/0021074 A1 | 1/2008 | Cartt |
| 2008/0035141 A1 | 2/2008 | Warner et al. |
| 2008/0038363 A1 | 2/2008 | Zaffaroni et al. |
| 2008/0045610 A1 | 2/2008 | Michalow |
| 2008/0057119 A1 | 3/2008 | Singh et al. |
| 2008/0064671 A1 | 3/2008 | Barlow et al. |
| 2008/0064725 A1 | 3/2008 | Basbaum et al. |
| 2008/0103105 A1 | 5/2008 | Barlow et al. |
| 2008/0103165 A1 | 5/2008 | Barlow et al. |
| 2008/0108574 A1 | 5/2008 | Barlow et al. |
| 2008/0131483 A1 | 6/2008 | Abdulrazik |
| 2008/0181943 A1* | 7/2008 | Cuine et al. ............... 424/456 |
| 2009/0291050 A1 | 11/2009 | Kordikowski et al. |
| 2010/0196286 A1 | 8/2010 | Armer et al. |
| 2010/0236547 A1 | 9/2010 | Cook |

FOREIGN PATENT DOCUMENTS

| | | |
|---|---|---|
| EP | 0 944 604 B1 | 1/2005 |
| EP | 1 813 285 A1 | 8/2007 |
| GB | 991589 A | 5/1965 |
| GB | 1076089 A | 7/1967 |
| WO | WO-94/27608 A1 | 12/1994 |
| WO | WO96-29066 | 9/1996 |
| WO | WO-97/32871 A1 | 9/1997 |
| WO | WO-98/23591 A1 | 6/1998 |
| WO | WO-98/23596 A1 | 6/1998 |
| WO | WO-98/23609 A1 | 6/1998 |
| WO | WO-98/23610 A1 | 6/1998 |
| WO | WO-98/23611 A1 | 6/1998 |
| WO | WO-98/23612 A1 | 6/1998 |
| WO | WO-98/46595 A1 | 10/1998 |
| WO | WO02-15883 | 2/2002 |
| WO | WO-02/094230 A1 | 11/2002 |
| WO | WO-2004/009090 A1 | 1/2004 |
| WO | WO-2004/010923 A2 | 2/2004 |
| WO | WO-2004/010923 A3 | 2/2004 |
| WO | WO-2004/060347 A2 | 7/2004 |
| WO | WO-2004/060347 A3 | 7/2004 |
| WO | WO-2004/078161 A1 | 9/2004 |
| WO | WO-2004/078163 A2 | 9/2004 |
| WO | WO-2004/078163 A3 | 9/2004 |
| WO | WO-2005/032519 A1 | 4/2005 |
| WO | WO-2006/036634 A2 | 4/2006 |
| WO | WO-2006/036634 A3 | 4/2006 |
| WO | WO-2006/061624 A1 | 6/2006 |
| WO | WO-2006/089082 A2 | 8/2006 |
| WO | WO-2006/089082 A3 | 8/2006 |
| WO | WO-2006/096434 A2 | 9/2006 |
| WO | WO-2006096434 A3 | 9/2006 |
| WO | WO-2007/025177 A2 | 3/2007 |
| WO | WO-2007/025177 A3 | 3/2007 |
| WO | WO-2007/025383 A1 | 3/2007 |
| WO | WO-2007/030697 A2 | 3/2007 |
| WO | WO-2007/030697 A3 | 3/2007 |
| WO | WO-2007/047978 A2 | 4/2007 |
| WO | WO-2007/047978 A3 | 4/2007 |
| WO | WO-2007/053596 A1 | 5/2007 |
| WO | WO-2007/100775 A2 | 9/2007 |
| WO | WO-2007/100775 A3 | 9/2007 |
| WO | WO-2007/104035 A1 | 9/2007 |
| WO | WO-2007/134077 A2 | 11/2007 |
| WO | WO-2007/134077 A3 | 11/2007 |
| WO | WO-2007/134136 A2 | 11/2007 |
| WO | WO-2007/134136 A3 | 11/2007 |
| WO | WO-2007/147556 A1 | 12/2007 |
| WO | WO-2008/003093 A2 | 1/2008 |
| WO | WO-2008/003093 A3 | 1/2008 |
| WO | WO-2008/024930 A2 | 2/2008 |
| WO | WO-2008/024930 A3 | 2/2008 |
| WO | WO-2008/030651 A1 | 3/2008 |
| WO | WO-2008/036678 A2 | 3/2008 |
| WO | WO-2008/036678 A3 | 3/2008 |
| WO | WO-2008/036846 A2 | 3/2008 |
| WO | WO-2008/036846 A3 | 3/2008 |
| WO | WO-2008/039863 A2 | 4/2008 |
| WO | WO-2008/039863 A3 | 4/2008 |

OTHER PUBLICATIONS

Lähdesmäki, J. et al. (2004, e-published Feb. 6, 2004). "Alpha2A-Adrenoceptors Are Important Modulators of the Effects of D-Amphetamine on Startle Reactivity and Brain Monoamines," *Neuropsychopharmacology* 29:1282-1293.

Trevor, A.J. et al. (2007). "Sedative-Hypnotic Drugs," Chapter 22 in *A Lange Medical Book: Basic & Clinical Pharmacology, Tenth Edition*, Katzung, B.G. ed., McGraw-Hill Companies, Inc. New York, NY pp. 347-362.

Valença, A.M. et al. (2004). "Clonidine in Respiratory Panic Disorder Subtype," *Arq Neuropsiquiatr* 62(2-B):396-398.

Venn, R.M. et al. (2000). "Respiratory Effects of Dexmedetomidine in the Surgical Patient Requiring Intensive Care," *Critical Care* 4(5):302-308.

Weinhouse, G.L. et al. (2006). "Sleep in the Critically Ill Patient," *Sleep* 29(5).707-716.

Wikipedia. (Jul. 31, 2008). "Alprazolam," located at <http://en.wikipedia.org/wiki/Alprazolam>, last visited on Jul. 31, 2008, 14 pages.

Wikipedia. (Jul. 22, 2008). "Clonidine," located at <http://www.en.wikipedia.org/wiki/Clonidine>, last visited on Aug. 7, 2008, 4 pages.

Wikipedia. (Jul. 28, 2008). "Dexmedetomidine," located at <http://en.wikipedia.org/wiki/Dexmedetomidine>, last visited on Jul. 31, 2008, 2 pages.

Wikipedia. (Jul. 22, 2008). "Eszopiclone," located at <http://en.wikipedia.org/wiki/Eszopiclone>, last visited on Jul. 31, 2008, 7 pages.

Wikipedia. (Jul. 14, 2008). "Ramelteon," located at <http://en.wikipedia.org/wiki/Ramelteon>, last visited on Jul. 31, 2008, 4 pages.

Wikipedia. (Jul. 14, 2008). "Zaleplon," located at <http://en.wikipedia.org/wiki/Zaleplon>, last visited on Jul. 31, 2008, 4 pages.

Wikipedia. (Jul. 27, 2008). "Zolpidem," located at <http://en.wikipedia.org/wiki/Zolpidem>, last visited on Jul. 31, 2008, 11 pages.

International Search Report mailed on Jan. 27, 2010, for PCT Patent Application No. PCT/US2009/066272, filed on Dec. 1, 2009, 3 pages.

(56) References Cited

OTHER PUBLICATIONS

International Search Report mailed on May 4, 2010, for PCT Patent Application No. PCT/US09/06688, filed on Dec. 21, 2009, two pages.
Written Opinion mailed on May 4, 2010, for PCT Application No. PCT/US09/06688, filed on Dec. 21, 2009, six pages.
Anttila et al., "Bioavailablity of dexmedetomidine after extravascular doses in healthy subjects", British Journal of Clinical Pharmacology, 56: 691-693 (2003), 3 pgs.
Berkenbosch et al., "Prospective evaluation of dexmedetomidine for noninvasive procedural sedation in children", Pediatric Critical Care Medicine, 6(4) 435-439 (Abstract) (2005), 2 pgs.
Iirola et al., "Bioavailability of dexmedetomidine after intranasal administration", European Journal of Clinical Pharmacology, 67:825-831 (2011), 7 pgs.
Nebulizer. The American Heritage Medical Dictionary, Houghton Mifflin Co. (2007) (accessed at www.xreferplus.com/entry.do?format=html&id=6584976).
Nelson et al., "The α2-Adrenoceptor Agonist Dexmedetomidine Converges on an Endogenous Sleep-promoting Pathway to Exert Its Sedative Effects", Anesthesiology 98(2) 428-436 (2003), 9 pgs.
Terajima et al., "Repeated dexmedetomidine infusions, a postoperative living-donor liver transplantation patient", Journal of Anesthesia, 20:234-236 (2006), 3 pgs.
Yuen et al., "A Double-Blind, Crossover Assessment of the Sedative and Analgesic Effects of Intranasal Dexmedetomidine", Anesthesia & Analgesia, 105(2): 374-380 (2007), 7 pgs.
Non-Final Office Action mailed Feb. 1, 2012, for U.S. Appl. No. 12/628,951, filed Dec. 1, 2009, 17 pages.
Response to Non-Final Office Action mailed Aug. 1, 2012, for U.S. Appl. No. 12/628,951, filed Dec. 1, 2009, 17 pages.
Knake et al. "Status Epilepticus: A Critical Review," (2009) Epilepsy & Behavior, v.15, pp. 10-14.
Martinez et al. "Prevalence of Acute Repetitive Seizures in the United Kingdom," (2009) Epilepsy Res., 87(203), pp. 137-143.
Riss et al. "Benzodiazepines in Epilepsy: Pharmacology and Pharmacokinetics," (2008) Acta Neurologica Scandinavica, 118(2), pp. 69-86.
Final Office Action mailed Jan. 3, 2013, for U.S. Appl. No. 12/628,951, filed Dec. 1, 2009, 26 pages.
Non-Final Office Action dated May 8, 2013, for U.S. Appl. No. 13/721,444, filed Dec. 20, 2012.

* cited by examiner

INHALATION DEVICES AND RELATED METHODS FOR ADMINISTRATION OF SEDATIVE HYPNOTIC COMPOUNDS

CROSS-REFERENCE TO RELATED APPLICATIONS

This application claims benefit of U.S. provisional application No. 61/203,560 filed 23 Dec. 2008 entitled "Inhalation Devices and Related Methods for Administration of Sedative Hypnotic Compounds" which is hereby incorporated by reference in its entirety.

FIELD

Described herein are formulations and devices for inhalation administration of sedative compounds. Specifically, formulations and devices that aerosolize sedative compounds for the treatment insomnia, including sleep onset and sleep maintenance are described. Methods and kits for treating insomnia are also described.

BACKGROUND

Insomnia is a common sleep disturbance that affects the quantity or quality of sleep. Insomnia may be acute (one to several nights) or chronic (months to years). The symptoms of insomnia are typically described as an inability to fall asleep (sleep onset insomnia) or remain asleep (sleep maintenance insomnia). In some instances, insomnia is associated with other medical conditions, such as anxiety and depression, or with use of certain medications. According to the National Sleep Foundation's Sleep in America Poll 2005, insomnia was a concern because the effects of sleep deprivation were reported to decrease the quality of life of the individual, and in some cases, compromise the safety and normal functioning of the individual in the workplace and while driving.

The current treatment of insomnia will vary depending on the etiology, nature, and severity of symptoms, and may include the use of pharmacologic agents. These agents typically are sedative compounds that include, but are not limited to: barbiturates, benzodiazepines, non-benzodiazepine sedatives (i.e. imidazopyridine class (zolpidem), pyrazolopyrimidine class (zaleplon) and pyrrolopyrazine class (eszopiclone)), $GABA_A$ receptor agonists, antihistamines, orexin receptor agonists, phenothiazines, melatonin, and melatonin MT1 and MT2 receptor agonists. As used herein, the terms "sedative", "hypnotic", "sedative hypnotic" and similar words or phrases are to be understood to be synonymous and refer to the ability to induce sleep.

Currently, oral nonbenzodiazepines such as Ambien® tablets (zolpidem tartrate) (Sanofi-Aventis, Bridgewater, N.J.), Lunesta® tablets (eszoplicone) (Sepracor, Marlborough, Mass.), and Sonata® capsules (zaleplon) (King Pharmaceuticals, Bristol, Tenn.).

Other nonbenzodiazapine treatments, all orally administered, which may include melatonin (OTC) and the melatonin receptor $MT_1/MT_2$ agonist Rozerem® tablets (ramelteon) (Takeda Pharmaceutical Co., Ltd., Osaka, Japan), are frequently prescribed for sleep disturbances.

Developmental compounds include the nonbenzodiazapine $GABA_A$ agonist, Indiplon (Neurocrine, San Diego, Calif.) and those with novel receptor activity such as HY10275 which is a dual-acting $H_1/5-HT_{2A}$ compound (Hypnion/Lilly, Lexington, Mass.) and almorexant, an orexin receptor antagonist (Actelion/GSK, Basel, Switzerland). These newer therapies minimize or avoid undesirable side effects typical of the $GABA_A$ agonists, such as memory impairment and dependence and abuse potential, tolerance and rebound insomnia.

All of these compounds are administered orally, and therefore can take from 1-2 hours to onset of therapeutic effects. Food or alcohol intake can significantly enhance or retard the therapeutic effects or time to onset. Because of the long time to onsets, the long duration of effects and the variability with GI loading, these therapies must be administered on a specific schedule hours before retiring for a normal sleep period. Because oral bioavailability can be low, relatively high doses are required to achieve and sustain systemic circulation concentrations sufficiently high to be effective, particularly for sleep maintenance. Such high dosage levels, combined with the long half lives of elimination typical of these compounds, result in long washout periods which can prolong residual sedation into normal waking hours.

Given the importance of the sedative-hypnotics in treating insomnia, an alternative to oral administration would be desirable to administer sedative hypnotics by means that would have rapid onset and could be administered just before retiring for normal sleep period. Devices for generating aerosols of sedative-hypnotic drugs for inhalation would enable rapid onset because therapeutically effective concentrations can be achieved rapidly by pulmonary administration. Additionally inhalation avoids interference from food or drink that is found with oral administration. Inhalation also bypasses first pass metabolism and results in higher bioavailability for small molecules such as the sedative-hypnotics. Therefore lower doses can be used to rapidly achieve therapeutic concentrations in systemic circulation in as fast as 2-3 minutes. The lower doses minimize side effects and residual sedation at the end of sleep period.

SUMMARY

The invention described herein includes formulations, methods, inhalation devices and kits for the treatment of sleep disturbances. The devices generally include a housing, an aerosol generating mechanism, and a sedative composition. The preferred inhalation device is a pressurized metered dose inhaler (pMDI). The pMDI may be breath-actuated.

The sedative compositions may include any barbiturates, benzodiazepines, non-benzodiazepine sedatives, $GABA_A$ receptor agonists, antihistamines, orexin receptor agonists, phenothiazines, melatonin, and melatonin $MT_1$ and $MT_2$ receptor agonists, $5-HT_{2A}$ antagonists, or combinations thereof that are useful for treating sleep disturbances. In addition to the sedative, excipients such as solvents, dispersants, preservatives, antioxidants, buffering agents, and flavoring agents may be used in the compositions. The sedative composition may be contained in pressurized metered dose inhaler (pMDI) within a pressurized reservoir fitted with a metering valve as a particle suspension or solution in a fluorocarbon propellant media.

The formulations, methods, and inhalation devices may be used to treat various sleep disturbances. For example, the formulations, methods, and inhalation devices may be used to treat insomnia, including acute insomnia, chronic insomnia, sleep onset insomnia, and sleep maintenance insomnia. In some embodiments of the invention, the aerosol generated by the inhalation device is capable of rapidly initiating sleep, thus decreasing sleep latency. As used herein, the terms "rapid" or "rapidly" refer to the induction of sleep within at least about 30 minutes after administration of the sedative. In other embodiments, the aerosol of the formulation is also capable of maintaining sleep for at least about 4 hours. In another embodiment, a drug combination may be administered, where one drug provides rapid induction of sleep, and the other drug provide longer-acting sedation for sleep maintenance, but not so long as to cause residual sedation at the end of the sleep period.

The inhalation devices may be disposable, single-use or multiple-use devices. They may also be packaged as kits including one or more inhalation devices and one or more sedative compositions. Here the sedative compositions may each include a different dose. The kits may also be tailored to the type of insomnia being treated.

DETAILED DESCRIPTION

Described herein are formulations, methods, inhalation devices and kits for treating sleep disturbances. As previously mentioned, the sleep disturbance that may be treated is insomnia, including without limitation, acute insomnia, chronic insomnia, sleep onset insomnia, and sleep maintenance insomnia. The inhalation devices will generally be configured to have a housing, an aerosol generating mechanism, and a sedative formulation. Said formulation, which includes at least one sedative-inducing medicament, when administered via pulmonary inhalation, preferably induces sleep in less than 30 minutes, more preferably further maintains that sleep for at least 4 hours and most preferably further limits that sleep so that there is little or no residual sedation after the normal sleep period. The dosage of each of the sedatives used is configured to provide a $T_{max}$ equal to or less than 20 minutes. In some variations, the devices include a dose counter and lock-out mechanism. Features that control airflow and/or plume deposition may also be employed.

I. DEVICES

The inhalation device may be of various designs, so long as they are capable of generating an aerosol of a sedative formulation for treating sleep disturbances. In the preferred embodiment, the inhalation device is a pMDI.

Pressurized Metered Dose Inhalers pMDIs generally have two components, a canister in which the drug formulation is stored under pressure as a suspension or a solution, and a receptacle which is used to hold and actuate the canister. The canister may contain multiple doses of the formulation, although it is possible to have single dose canisters as well. The canister typically includes a valved outlet from which the contents of the canister can be discharged. Aerosolized drug is dispensed from the pMDI by applying a force on the canister to push it into the receptacle thereby opening the valved outlet and causing the drug formulation to be conveyed from the valved outlet through the receptacle outlet. Upon discharge from the canister, the drug formulation is atomized, forming an aerosol containing the medicament. pMDIs use propellants to pressurize the contents of the canister and to propel the drug formulation out of the receptacle outlet. In pMDIs, the composition may be provided in liquid form, and resides within the canister along with the propellant. The composition can also be a solution wherein the medicament is soluble in the propellant alone or in combination with one or more co-solvents. The propellant may take a variety of forms. For example, the propellant may be a compressed gas or liquefied gas. In the past, commonly used liquid propellants included chlorofluorocarbons (CFC) which are now banned. CFCs have almost completely been replaced by hydrofluororalkane (HFA) propellants.

In some instances, the discharge of aerosolized drug must be coordinated with inhalation, so that the aerosolized drug is entrained within the inspiratory air flow and conveyed to the lungs. In other instances, a breath-actuated trigger, such as that included in the Tempo® inhaler (MAP Pharmaceuticals, Mountain View, Calif.) may be employed that automatically discharges a dose of drug upon sensing inhalation.

Detailed descriptions of the Tempo® inhaler may be found, for example, in U.S. Pat. Nos. 5,954,047; 6,026,808; 6,095,141; and 6,367,471 which are hereby incorporated by reference in their entirety.

II. COMPOUNDS

The present invention is the treatment or reduction in symptoms of the various sleep disturbances described herein by administering via pulmonary inhalation formulation incorporating various medicaments which can include but are not limited to barbiturates, benzodiazepines, non-benzodiazepines, $GABA_A$ receptor agonists, antihistamines, orexin receptor agonists, phenothiazines, melatonin, melatonin $MT_1$ and melatonin $MT_2$ receptor agonists, their derivatives, and combinations thereof, as described herein.

Specifically, barbiturates include without limitation amobarbital, butobarbital and secobarbital. Benzodiazepine site modulators such as GABA-receptor agonists may be used. Suitable GABA receptor agonists that may be employed include without limitation, cyclopyrrolones such as eszopiclone, pyrazolopyrimidines such as zaleplon, imidazo[1,2-a]pyrimidines such as zolpidem, combinations, salts, acids, derivatives, and analogs thereof. The GABA-receptor agonists may have short-acting or long-acting effects.

Eszopiclone is a short-acting nonbenzodiazapine hypnotic agent. It is the dextrorotatory isomer of 6-(5-chloro-2-pyridyl)-5[(4-methyl-1-piperazinyl)carbonyloxy]-7-oxo-6,7-di hydro-5H-pyrrolo[3,4-b]pyrazine, also known as zopiclone. Properties of eszopiclone and its pharmaceutically acceptable salts, salts of organic acids, organic acids, and derivatives thereof, as well as the preparation of these compounds are disclosed in U.S. Pat. Nos. 6,319,926; 6,864,257; 6,444,673; 6,864,257; 7,125,874; and 7,381,724.

Zaleplon is also a short-acting nonbenzodiazepine hypnotic agent. It is also known as (N-[3-(3-cyanopyrazolo[1,5a] pyrimidin-7-yl)phenyl]-N-ethylacetamide). Properties of zaleplon as well as its preparation are disclosed in U.S. Pat. No. 4,626,538. A crystalline form of zaleplon, which may also be employed in the compositions described herein, is described in U.S. Publication No. 2002/0072527.

Zolpidem is another short-acting nonbenzodiazepine hypnotic agent. It is also known as N,N,6-trimethyl-2-(4-methylphenypimidazo[1,2-a]pyridine-3-acetamide. Properties of zolpidem and its pharmaceutically acceptable salts and derivatives, as well as the preparation of these compounds are disclosed in GB Nos. 991,589 and 1,076,089, and U.S. Pat. Nos. 4,382,938; 4,460,592; 4,492,695; and 6,242,460.

In another embodiment of the invention, a melatonin receptor agonist is used to treat sleep disturbances. A suitable melatonin receptor agonist is ramelteon, which is a hypnotic agent, chemically designated as (S)-N-[2-(1,6,7,8-tetrahydro-2H-indeno-[5,4-b]furan-8-yl)ethyl]propionamide. Properties of ramelteon and its pharmaceutically acceptable salts and derivatives, as well as the preparation of these compounds are disclosed in U.S. Pat. No. 6,034,239 and WO 97/32871. Other examples of a suitable melatonin receptor agonist include melatonin itself, Rozerem® (Takeda), tasimelteon aka VEC-162 (Vanda Pharmaceuticals, Inc.) and drugs acting on the serotonin system such as Eplivanserin (Sanofi-Aventis).

In another embodiment of the invention, antihistamines are used to treat sleep disturbances. Antihistamines are classically understood to function as histamine agonists and especially those that act on the $H_1$ receptor. Antihistamines can include, but are not limited to diphenhydramine, loratadine, desloratadine, meclizine, fexofenadine, pheniramine, cetirizine, and promethazine In another embodiment of the invention, phenothiazines are used in the formulation of the invention to treat sleep disturbances. This class of compounds is based upon the parent compound phenothiazine, which is a yellow tricyclic compound which is soluble in acetic acid, benzene, and ether. Phenothiazine derivatives are classified into three groups that differ with respect to the substituent on the sole nitrogen atom: the aliphatic compounds (bearing acyclic groups), the "piperidines" (bearing piperidine-derived groups), and the piperazine (bearing piperazine-derived substituents). Phenothiazines can include, but are not limited to promazine, chlorpromazine, mesoridazine, thioridazine, perphenazine and flupexitxol.

In another embodiment of the invention, orexin receptor is used in the formulation of the invention to treat sleep disturbances. Such antagonists could include almorexant which is being developed by Actelion Pharmaceuticals LTD as an oral therapy.

In another embodiment of the invention, a $5\text{-}HT_{2A}$ antagonist is used in the formulation of the invention to treat sleep disturbances.

III. PHARMACEUTICAL COMPOSITIONS AND DOSAGE FORMS

In some embodiments of the invention, the sedative formulations of the invention may include a benzodiazepine site modulator, as described above. Benzodiazepine site modulators directly or indirectly bind to the GABA (gamma-aminobutyric acid) receptor to potentiate the action of GABA (an inhibitory neurotransmitter). Examples of benzodiazepine site modulators that may be used in the sedative compositions include, but are not limited to eszopiclone, zaleplon, zolpidem, combinations, and salts, acids, derivatives, and analogs thereof. The compositions may also contain one or more inactive substances such as antioxidants, buffers, preservatives, flavoring agents, etc. Depending on the whether the composition is a solution, dispersion, or a suspension, pharmaceutically acceptable solvents, propellants, carriers, dispersants, etc., may also be used.

In other embodiments of the invention, the sedative formulations of the invention, described herein, may include a melatonin receptor agonist. Here the composition may also include one or more inactive substances such as antioxidants, buffers, preservatives, flavoring agents, etc. As also mentioned above, depending on the whether the composition is a solution, dispersion, or suspension, pharmaceutically acceptable solvents, propellants, carriers, dispersants, etc., may be used.

In yet further embodiment of the invention, the sedative formulation of the invention may include combinations of benzodiazepine site modulators, a combination of a benzodiazepine site modulator and a benzodiazepine or a melatonin receptor agonist, or a combination of a melatonin receptor agonist and a benzodiazepine. The combination therapy may be useful when an individual suffers from both sleep onset insomnia and sleep maintenance insomnia because a rapid and/or short-acting agent may be used with a longer-acting agent. For example, eszopiclone may be combined with zaleplon.

The following table contains examples of some of medicaments that could be used in formulations of the present invention.

| Drug | Half Life (hours) | Duration of Action (hours) |
| --- | --- | --- |
| Chlordiazepoxide | 7-13 | 24-28 |
| Diazepam | 30-56 | 24-28 |
| Flurazepam | 50-100 | 24-28 |
| Lorazepam | 9-19 | 12-18 |
| Oxazepam | 6-10 | 12-18 |
| Temazepam | 5-17 | 12-18 |
| Triazolam | 2-4 | <6 |
| Alprazolam | 9-14 | <6 |
| Midazolam | 1.3-2.5 | 4 |
| Lormetazepam | 10 | 12-18 |
| Nitrazepam | 28 | 24 |
| Clonazepam | 18-28 | 24-28 |
| Zolpidem | 2 | <4 |
| Eszopiclone | 6 | 8 |

When a benzodiazepine is used in the sedative formulation of the invention, exemplary benzodiazepines that may be employed include, but are not limited to alprazolam, bromazepam, camazepam, chlordiazepoxide, clobazam, clorazepic acid, clotiazepam, cloxazolam, diazepam, ethyl loflazepate, etizolam, fludiazepam, flutazolam, flutoprazepam, halazepam, ketazolam, lorazepam, medazepam, metaclazepam, mexazolam, nordazepam, oxazepam, oxazolam, pinazepam, prazepam, tofisopam, salts, acids, derivatives, and analogs thereof.

In another embodiment of the invention, the sedative formulation of the invention is a liquid composition for use with a pMDI, and may include a benzodiazepine site modulator or a melatonin receptor agonist, a propellant and/or one or more cosolvents, surface modifying agents or surfactants. Suitable propellants include, but are not limited to, dichlorodifluoromethane, trichlorofluoromethane, dichlorotetrafluoroethane, and hydrofluoroalkanes. Hydrofluoroalkanes include 1,1,1,2-tetrafluoroethane or 1,1,1,2,3,3,3-heptafluoropropane.

A further embodiment would include a benzodiazepine site modulator, a melatonin receptor agonist, and benzodiazepine. Any amount of the benzodiazepine site modulator, melatonin receptor agonist, and benzodiazepine may be included in the sedative compositions. For example, they may be included in amounts of about 1% to about 99% by weight of the composition. In one embodiment, the active agents are included in an amount of about 1% to about 90% by weight, about 1% to about 80% by weight, about 1% to about 70% by weight, about 1% to about 60% by weight, about 1% to about 50% by weight, about 1% to about 40% by weight, about 1% to about 30% by weight, about 1% to about 20% by weight, about 1% to about 10% by weight, or about 1% to about 5% by weight of the composition. It is understood that the above amounts are exemplary, and that there may be instances in which higher or lower amounts may be used.

IV. METHODS OF ADMINISTRATION

The sedative formulations described here may be administered by inhalation using devices such as a pMDI with or without a breath-actuation feature. In general, a user first completely exhales and then inhales through the mouthpiece, establishing air flow through the device. In the case of a breath actuated device, the device will automatically discharge the drug after the user begins to inhale. In the case of a conventional pMDI device, the user will press the canister to discharge a dose and simultaneously inhale to administer the dose. In either case, the user continues to inhale to fill their lungs to capacity after the discharge and then may hold their breath for a period of time to allow the aerosolized drug to settle within the airways of the lungs.

The active agents in the sedative formulations may be provided in many dosage ranges. For example, each inhalation may provide a dose from about 0.05 mg to about 20 mg of the active agent. In some embodiments, the dose may range from about 0.25 mg to about 10 mg. In other embodiments, the dose may range from about 1.0 mg to about 7.0 mg. In further embodiments, the dose may range from about 2.0 mg to about 5.0 mg of the active agent.

The dosing regimen employed may depend on a number of factors, such as the type of insomnia being treated, particular active agent being used, severity of symptoms, and whether the insomnia is due to an underlying medical condition. In general, the sedative composition may be administered once a day when sleep is desired. However, administration may be repeated if it safe to do so. In some embodiments the drug may be administered at the start of the normal sleep period and can be administered again if the user awakens in the middle of the sleep period.

V. KITS

The inhalation devices and sedative compositions may be provided in a kit. The kits may contain devices containing one or more of the sedatives described herein. In one particular embodiment, the kit would include an inhalation device as described herein; the sedative formulation would include a benzodiazepine site modulator or melatonin receptor agonist, or a combination thereof. Some kits will include one or more sedative formulations and one or more pMDIs. The included compositions may contain the active agents in the same or different doses. Instructions may be in printed, included photographs, and/or pictographic depictions of how to use the device. In addition, the instruction can be on recorded media including audio tape, audio CD, video tape, DVD, CD-ROM, or the like.

The kits can be designed to target specific types of insomnia. In one embodiment, the kit is designed for use with sleep onset insomnia. Such a kit may include one or more short-acting agents. In another variation, the kit is designed for use with sleep maintenance insomnia, which may include both a short-acting agent in addition to a long-acting agent.

VI. EXAMPLES

Pressurized Metered Dose Inhaler Examples

Example 1

Zolpidem 71.25 mg zolpidem
14.25 mL hydrofluoroalkane propellant (HFA-134a or HFA-227 or a mixture thereof)
19 mL aluminum canister with or without a polymeric coating.
A closure system with a metering chamber capable of metering fixed volumes. For instance, a 100 mcL valve used in conjunction with the above formulation and components would emit a dose of zolpidem approximately equal to 0.5 mg.

Example 2

Zaleplon 142. 5 mg zaleplon
14.25 mL hydrofluoroalkane propellant (HFA-134a or HFA-227 or a mixture thereof)
19 mL aluminum canister with or without a polymeric coating.
A closure system with a metering chamber capable of metering fixed volumes. For instance, a 100 mcL valve used in conjunction with the above formulation and components would emit a dose of zalepon approximately equal to 1 mg.

Example 3

Ramelteon

Ramelteon is typically administered by oral tablet, and the active agent is converted to the major metabolite in the liver. Oral bioavailability of ramelteon is 1.8% due to extensive hepatic transformation. The metabolite, MII, is less active but circulates at higher concentrations, and may also be a more potent carcinogen.

As pulmonary delivery bypasses first pass metabolism, doses can be lower. Considering a mean functional activity of MII at 21 times lower potency than ramelton, typical inhaled doses entering the systemic circulation of ramelteon would need to be in the 0.25-2 mg range, ideally 0.5 mg Therefore, a suitable pMDI formulation would be as follows:

50 mg ramelteon
10 mL hydrofluoroalkane propellant (HFA-134a or HFA-227 or a mixture thereof)
14 mL aluminum canister with or without a polymeric coating.
A closure system with a metering chamber capable of metering fixed volumes. For instance, a 100 mcL valve used in conjunction with the above formulation and components would emit a dose of ramelteon approximately equal to 0.5 mg.

Example 4

Eplivanserin 200 mg eplivanserin
8.95 mL hydrofluoroalkane propellant (HFA-134a or HFA-227 or a mixture thereof)
10 mL aluminum canister with or without a polymeric coating.
A closure system with a metering chamber capable of metering fixed volumes. For instance, a 100 mcL valve used in conjunction with the above formulation and components would emit a dose of eplivanserin approximately equal to 2 mg.

While certain embodiments have been described herein, it will be understood by one skilled in the art that the methods, systems, and apparatus of the present disclosure may be embodied in other specific forms without departing from the spirit thereof. The present embodiments are therefore to be considered in all respects as illustrative and not restrictive of the present disclosure. Rather, the scope and spirit of the present invention is embodied by the appended claims.

What is claimed is:

1. A device for treating a sleep disturbance in a patient in need of such treatment, by pulmonary inhalation of a formulation, said device comprising:
   a sedative formulation;
   a pressurized metered dose inhaler (pMDI) adapted to administer said sedative formulation to the airways of the lungs via pulmonary inhalation; and
   wherein the formulation can induce sleep within 30 minutes of administration to the patient.

2. The device as described in claim 1 wherein said formulation comprises one or more sedatives selected from the group consisting of a barbiturate, a benzodiazepine, a non-benzodiazepine, a GABA receptor agonists, an antihistamine, an orexin receptor agonist, a phenothiazine, a melatonin $MT_1$ receptor agonist, a melatonin $MT_2$ receptor agonist, and a $5\text{-}HT_{2A}$ antagonist.

3. The device as described in claim 2 wherein said formulation comprises one or more sedatives selected from the group consisting of zolpidem, zalepon, remelteon, eszopiclone, and eplivanserin.

4. The device as described in claim 3 wherein said formulation causes minimal or no residual sedation after the patient awakes from the induced sleep.

5. The device as described in claim 2 wherein said formulation can maintain sleep for 4-6 hours after inducing sleep.

6. The device as described in claim 2 wherein said formulation comprises two or more sedatives wherein at least one of said sedatives is a short acting sedative and wherein one or more of said sedatives is a long acting sedative.

7. The device as described in claim 2 wherein each activation of said pMDI delivers from said pMDI about 0.05 milligrams to about 20.0 milligrams of total sedative.

8. The device as described in claim 2 wherein an effective therapeutic dose of said formulation is delivered in one or more activations of said pMDI.

9. The device as described in claim 2 wherein the $T_{max}$ of one or more of said sedatives is equal to or less than about 20 minutes.

10. The device as described in claim 2 wherein the one or more sedatives is in a solution.

11. The device as described in claim 2 wherein the one or more sedatives is in a suspension.

12. A method for treating a sleep disturbance in a patient in need of such treatment said method comprising the steps of:
   administering to the patient a sedative formulation to the airways of the lungs via pulmonary inhalation using a pressurized metered dose inhaler (pMDI);
   wherein the sedative formulation can induce sleep within 30 minutes of administration;
   thereby inducing sleep in the patient.

13. The method as described in claim 12 wherein said sedative formulation comprises one or more sedatives selected from the group consisting of a barbiturate, a benzodiazepine, a non-benzodiazepine, a GABA receptor agonists, an antihistamine, an orexin receptor agonist, a phenothiazine, a melatonin $MT_1$ receptor agonist, a melatonin $MT_2$ receptor agonist, and a $5\text{-}HT_{2A}$ antagonist.

14. The method as described in claim 13 wherein said formulation comprises one or more sedatives selected from the group consisting of zolpidem, zaleplon, ramelteon, eszopiclone and eplivanserin.

15. The method as described in claim 13 wherein said formulation comprises a solution of the one or more sedatives.

16. The method as described in claim 13 wherein said formulation comprises a suspension of the one or more sedatives.

17. The method as described in claim 12 wherein said formulation can maintain sleep for 4-6 hours after inducing sleep.

18. The method as described in claim 12 wherein said formulation causes minimal or no residual sedation after the patient awakes from the induced sleep.

19. The method as described in claim 12 wherein said formulation comprises two or more sedatives wherein at least one of said sedatives is a short acting sedative and wherein one or more of said sedatives is a long acting sedative.

20. The method as described in claim 12 wherein each activation of the pMDI delivers from said device about 0.05 milligrams to about 20.0 milligrams of total sedative.

21. The method as described in claim 12 wherein an effective therapeutic dose of said formulation is delivered in one or more activations of the pMDI.

22. The method as described in claim 12 wherein the $T_{max}$ of one or more of said sedatives is equal to or less than about 20 minutes.

23. A kit for treating a sleep disturbance in a patient in need of such treatment, by pulmonary delivery of a sedative formulation, said kit comprising:
   a sedative formulation in a pressurized metered dose inhaler (pMDI) adapted to administer said sedative formulation to the airways of the lungs via pulmonary inhalation; wherein the sedative formulation can induce sleep within 30 minutes of administration;
   instructions for the use of said pMDI; and
   a container for holding all other components of the kit.

* * * * *

UNITED STATES PATENT AND TRADEMARK OFFICE
CERTIFICATE OF CORRECTION

PATENT NO.         : 8,555,875 B2                                        Page 1 of 1
APPLICATION NO.    : 12/655076
DATED              : October 15, 2013
INVENTOR(S)        : Robert Owen Cook et al.

It is certified that error appears in the above-identified patent and that said Letters Patent is hereby corrected as shown below:

On title page 3, in column 1, item (56) under "Other Publications", line 6, delete "Bioavailablity" and insert -- Bioavailability --, therefor.

In the Specification

In column 1, line 47, delete "MT1 and MT2" and insert -- $MT_1$ and $MT_2$ --, therefor.

In column 1, line 53, delete "(eszoplicone)" and insert -- eszopiclone --, therefor.

In column 1, line 56, delete "nonbenzodiazapine" and insert -- nonbenzodiazepine --, therefor.

In column 1, lines 61-62, delete "nonbenzodiazapine" and insert -- nonbenzodiazepine --, therefor.

In column 3, line 65, delete "hydrofluororalkane" and insert -- hydrofluoroalkane --, therefor.

In column 3, line 47, delete "Costridial" and insert -- Clostridial --, therefor.

In column 4, line 32, delete "nonbenzodiazapine" and insert -- nonbenzodiazepine --, therefor.

In column 4, lines 34-35, delete "di hydro" and insert -- dihydro --, therefor.

In column 4, lines 49-50, delete "(4-methylphenypimidazo" and insert -- (4-methylphenyl)imidazo --, therefor.

In column 5, line 7, delete "promethazine" and insert -- promethazine. --, therefor.

In column 5, line 20, delete "flupexitxol." and insert -- flupentixol. --, therefor.

In column 8, line 13, delete "zalepon" and insert -- zaleplon --, therefor.

In column 8, line 28, delete "ramelton," and insert -- ramelteon --, therefor.

In column 8, line 30, delete "0.5 mg" insert -- . --.

In the Claims

In column 9, line 19, in claim 3, delete "zalepon, remelteon," and insert -- zaleplon, ramelteon, --, therefor.

Signed and Sealed this
Twenty-fifth Day of February, 2014

Michelle K. Lee
*Deputy Director of the United States Patent and Trademark Office*